US012780898B2

(12) United States Patent
Kassam et al.

(10) Patent No.: US 12,780,898 B2
(45) Date of Patent: Nov. 3, 2026

(54) METHODS AND DEVICES FOR COMPLEXING TARGET ENTITIES

(71) Applicant: STEMCELL Technologies Canada Inc., Vancouver (CA)

(72) Inventors: Adil Kassam, Vancouver (CA); Eric Jervis, Vancouver (CA)

(73) Assignee: Stemcell Technologies Canada Inc., Vancouver (CA)

( * ) Notice: Subject to any disclaimer, the term of this patent is extended or adjusted under 35 U.S.C. 154(b) by 663 days.

(21) Appl. No.: 18/352,717

(22) Filed: Jul. 14, 2023

(65) Prior Publication Data

US 2023/0374106 A1 Nov. 23, 2023

Related U.S. Application Data

(62) Division of application No. 16/912,882, filed on Jun. 26, 2020, now Pat. No. 11,725,042.

(Continued)

(51) Int. Cl.

| | |
|---|---|
| ***C07K 14/705*** | (2006.01) |
| ***A61K 47/69*** | (2017.01) |
| ***C07K 16/28*** | (2006.01) |
| ***C12M 1/00*** | (2006.01) |
| ***C12M 1/12*** | (2006.01) |
| ***C12M 1/34*** | (2006.01) |
| ***G01N 33/48*** | (2006.01) |
| ***G01N 33/50*** | (2006.01) |
| ***G01N 33/53*** | (2006.01) |
| ***G01N 33/537*** | (2006.01) |
| ***G01N 33/541*** | (2006.01) |
| ***G01N 33/543*** | (2006.01) |

(Continued)

(52) U.S. Cl.

CPC .... *C07K 14/70596* (2013.01); *A61K 47/6913* (2017.08); *C07K 16/2896* (2013.01); *C12M 21/00* (2013.01); *C12M 25/14* (2013.01); *C12M 41/36* (2013.01); *G01N 33/48* (2013.01); *G01N 33/50* (2013.01); *G01N 33/53* (2013.01); *G01N 33/537* (2013.01); *G01N 33/541* (2013.01); *G01N 33/54346* (2013.01); *G01N 33/566* (2013.01); *G01N 33/577* (2013.01); *C07K 2319/03* (2013.01); *G01N 2333/705* (2013.01); *G01N 2333/70596* (2013.01)

(58) Field of Classification Search

CPC .......... C07K 14/70596; C07K 16/2896; C07K 2319/03; C12M 21/00; C12M 25/14; C12M 41/36; A61K 47/6913; G01N 33/48; G01N 33/50; G01N 33/53; G01N 33/537; G01N 33/541; G01N 33/54346; G01N 33/566; G01N 33/577; G01N 2333/705; G01N 2333/70596

See application file for complete search history.

(56) References Cited

U.S. PATENT DOCUMENTS

| | | | |
|---|---|---|---|
| 6,448,075 B1 | 9/2002 | Thomas et al. | |
| 10,220,332 B2 * | 3/2019 | Gjerde | B01D 15/14 |

FOREIGN PATENT DOCUMENTS

| | | |
|---|---|---|
| WO | 2019014486 A1 | 1/2019 |

OTHER PUBLICATIONS

Diagenode ExoIP kit user manual; Oct. 23, 2015 (13 total pages).

(Continued)

*Primary Examiner* — Kathryn Elizabeth Limbaugh

(74) *Attorney, Agent, or Firm* — Smart & Biggar LP; Micheline Gravelle

(57) ABSTRACT

A device for recovering a population of extracellular vesicles from a biological sample comprising extracellular vesicles and contaminants is described.

11 Claims, 6 Drawing Sheets

Related U.S. Application Data

(60) Provisional application No. 62/867,434, filed on Jun. 27, 2019.

(51) Int. Cl.
*G01N 33/566* (2006.01)
*G01N 33/577* (2006.01)

(56) References Cited

OTHER PUBLICATIONS

Hildonen et al. Isolation and mass spectrometry analysis of urinary extraexosomal proteins. Scientific Reports 6: 36331, 2016 (15 total pages).

JSR Life Sciences ExoCap user manual; Jun. 19, 2015 (9 total pages).

Konoshenko et al. Isolation of extracelluar vesicles: general methodologies and latest trends. Biomed Res Internat 2018: 8545347 (28 total pages).

Li et al. Progress in exosome isolation techniques. Theranostics 7(3): 789-804, 2017.

Lim et al. Direct isolation and characterization of circulating exosomes from biological samples using magnetic nanowires. J Nanobiotechnol 17: 1, Jan. 7, 2019.

MBL ExoCap Product Catalog 2017.

Sharma et al. Immunoaffinity-based solution of melanoma cell-derived exosomes from plasma of patients with melanoma. J Extracell Vesicles 7: 1435138, 2018.

Willms et al. Extracellular vesicle heterogeneity: subpopulations, isolation techniques, and diverse functions in cancer progression. Front Immunol 9: 738, 2018.

* cited by examiner

METHODS AND DEVICES FOR COMPLEXING TARGET ENTITIES

CROSS-REFERENCE TO RELATED APPLICATIONS

This application is a divisional of U.S. patent application Ser. No. 16/912,882, filed Jun. 26, 2020 (now allowed), which claims the benefit under 35 USC § 119(e) from U.S. Provisional Application No. 62/867,434, filed on Jun. 27, 2019, all of which are incorporated herein by reference in their entirety.

TECHNICAL FIELD

This disclosure relates to biological assays, and more specifically biological assays for recovering target entities. In particular, this disclosure relates to the recovery of target entities from a sample that may also comprise contaminants.

BACKGROUND

Extracellular Vesicles (EVs) are commonly classified into two categories: microvesicles and exosomes. Microvesicles are derived from plasma membrane and exosomes are derived from endosomal pathway.

Tetraspanins such as CD9, CD63, and CD81 are enriched in EV surface. Common isolation methods include differential ultracentrifugation, polymer precipitation, size exclusion, etc.

There is a need in the field for methods and devices that specifically/selectively and rapidly recover target entities, such as EVs, from heterogeneous samples. Further, the types and numbers of components added to samples to effect target entity recovery should be minimized in such methods and devices.

SUMMARY

The present disclosure relates to methods and devices for recovering a population of target entities from a sample comprising target entities and contaminants. In some embodiments, a sample may also include non-target entities.

In one aspect of this disclosure are provided methods of recovering a population of target entities from a sample comprising target entities and contaminants. Steps of the methods include removing from the sample contaminants that are relatively larger or more dense and/or relatively smaller or less dense than the target entities, contacting the sample with a plurality of binding compositions, each binding composition having first and/or second moieties capable of binding with a recognition motif of the target entities under conditions to allow complexing the target entities with the plurality of binding compositions to form a complexed population of target entities, the complexed population of target entities having an altered physical property in comparison to the target-entities in individual form, and recovering the complexed population of target entities.

In some embodiments, the complexed population of target entities is homotypic.

In some embodiments, the first and second moieties interact with the same or different recognition motif. In some embodiments the recognition motif is one or more of CD9, CD63, and CD81.

In some embodiments, the first and second moieties are antibodies or fragments thereof. In some embodiments, the first and second moieties are held together by third and fourth moieties. In some embodiments, the third and fourth moieties are antibodies or fragments thereof.

In some embodiments, the plurality of binding compositions are at below-saturation levels.

In some embodiments, the sample further comprises non-target entities.

In some embodiments, the methods further comprise after the target entities are complexed with the plurality of binding compositions, fractionating the complexed population of target entities from non-target entities.

In some embodiments, the methods further comprise after fractionating the complexed population of target entities from non-target entities, recovering specifically the fractionated non-target entities. In some embodiments, recovering specifically the fractionated non-target entities comprises complexing the fractionated non-target entities with a second plurality of binding compositions to form a complexed population of non-target entities, the complexed population of non-target entities having an altered physical property in comparison to the target-entities in individual form.

In some embodiments, the contaminants may include one or more of cells, cellular debris, organelles, macromolecules, or breakdown products of any of the foregoing. In some embodiments, the macromolecules may include one or more of a lipid, a nucleic acid, a protein, or a carbohydrate.

In some embodiments, the sample is a biological sample.

In some embodiments, the target entities are extracellular vesicles or exosomes.

In some embodiments, the non-target entities are extracellular vesicles or exosomes.

In another aspect of this disclosure is a device for recovering a population of target entities from a sample comprising target entities and contaminants. Features of the device include a first porous unit having a first pored member flanked by a first inlet and a first outlet, a second porous unit having a second pored member flanked by a second inlet and a second outlet, the second porous unit positioned downstream of and in fluid communication with the first porous unit, a chamber between the first porous unit and the second porous unit, and a plurality of binding compositions loaded or loadable in the chamber, each binding composition having first and second moieties capable of interacting with a recognition motif of the target entities, wherein the plurality of binding compositions complex the target entities to form a complexed population of target entities.

In some embodiments, a pore size of the first pored member is impervious to large contaminants in the sample, and a pore size of the second pored member is impervious to the complexed population of target entities. In some embodiments, the pore size of the first pored member is impervious to the complexed population of target entities.

In some embodiments, the plurality of binding compositions are at below-saturation levels.

In some embodiments, the first and second moieties bind the same or different recognition motif. In some embodiments, the first and second moieties are antibodies or fragments thereof.

In some embodiments, the first and second moieties are held together by third and fourth moieties. In some embodiments, the third and fourth moieties are antibodies or fragments thereof.

In some embodiments, the plurality of binding compositions in the chamber are lyophilized.

In some embodiments, the device may further comprise an outlet means from the chamber.

In some embodiments, the first outlet and the second inlet are connectable thereby forming the chamber.

In some embodiments, the device may further comprise a housing enclosing the chamber.

In some embodiments, the sample further comprises non-target entities.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

Embodiments of the application will now be described in greater detail with reference to the attached figures in which.

DETAILED DESCRIPTION

Figure 1:
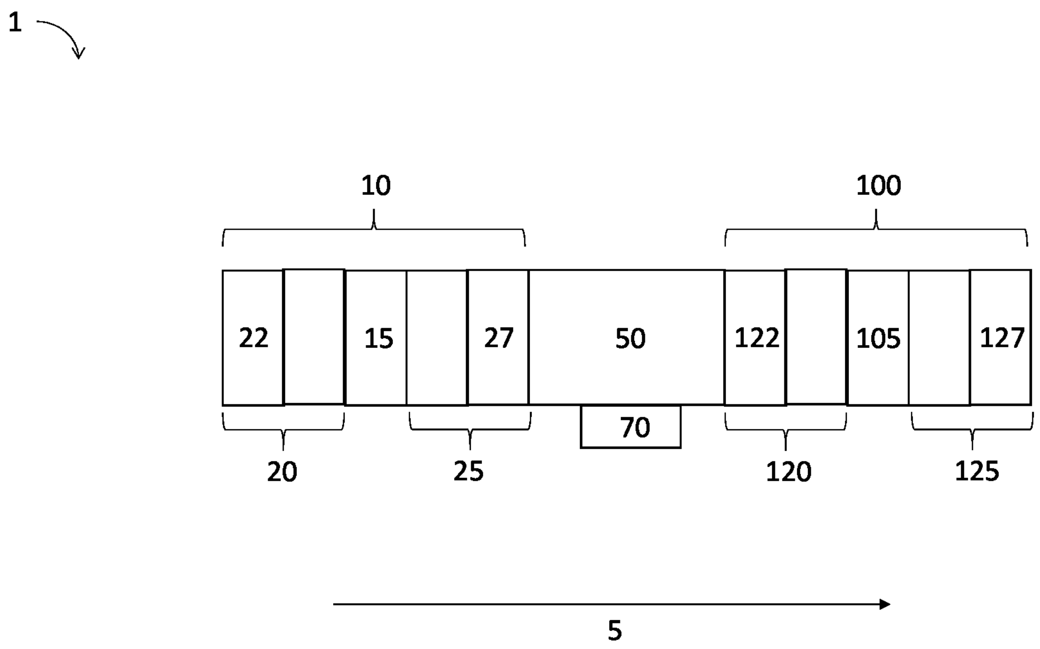
FIG. 1 shows a diagram of one embodiment of a device for recovering a population of target entities from a sample.

The present disclosure relates to methods and devices for recovering a population of target entities from a sample comprising target entities and contaminants.

Where used herein, "target entities" refers to those features within a sample intended to be specifically recovered or isolated therefrom. Target entities will present one or more recognition motifs on a surface thereof that distinguish targets from other components of a sample. Thus, target entities may be recovered with reliance on such one or more recognition motifs. Target entities may be cells or some part(s) thereof, such as organelles. In one embodiment target entities may be mammalian cells, or a specific type of cell. For example, the mammalian cells may be CD3+ cells. Target entities may also be cell products, such as macromolecules (e.g. proteins or nucleic acids), or extracellular vesicles, such as microvesicles or exosomes.

In some embodiments, target entities are extracellular vesicles. In one embodiment the target entities are micorvesilces or exosomes, or more specifically mammalian micorvesilces or exosomes. In some embodiments, the extracellular vesicles may present one or more recognition motifs, which are known in the art or may become known in the art. Examples of known recognition motifs of extracellular vesicles include: CD9, CD63, CD81, CD82, CD47, heterotrimeric G proteins, MHC class I, integrins, transferrin receptor, LAMP1/2, heparin sulfate proteoglycans, syndecans, EMMPRIN, ADAM10, GPI-anchored 5'nucleotidase CD73, complement-binding protein CD55 and CD59, sonic hedgehog, TSPANs, CD37, CD53, PECAM1, ERBB2, EPCAM, CD90, CD45, CD41, CD42a, Glycophorin A, CD14, MHC class II, CD3, acetylcholinesterase, amyloid beta A4/APP, multidrug resistance-associated protein ABCC1. In one embodiment, the one or more recognition motifs may include CD9, CD63, CD81, or any combination thereof. If all of CD9+, CD63+, and CD81+ are target entities intended to be recovered from a sample, this may be referred as the "pan-EV" condition.

Where used herein, "sample" refers to any potential source of target entities. The sample may be a chemical sample, such as when target entities may be chemically synthesized. Or, the sample may be a biological sample, including but not limited to a tissue or bone marrow, blood whether whole or otherwise, urine, cerebrospinal fluid, saliva, or cell culture medium whether or not conditioned by extracellular vesicle- or exosome-producing cells or tissues. In one embodiment the sample is a mammalian biological sample. To facilitate recovery of target entities, the sample is preferably fluid, and more preferably liquid.

A sample may also include contaminants, which may be characterized as objects other than the target entities present in a sample. Indeed, the concept of contaminants within the scope of this disclosure is relative to the nature of the target intended to be recovered from the sample. If for example, the target entities are cells then the contaminants may include other objects present in a sample, such dead cells, cell products, and cellular debris. If for example, the target entities are extracellular vesicles, such as microvesicles or exosomes then the contaminants may include other objects present in a sample, such as live or dead cells, cell products (other than extracellular vesicles or exosomes), and cellular debris. While the contaminants contemplated herein may not be biologically harmful, they may pose harm in the sense that their presence may reduce the efficiency of target entity recovery. Indeed, contaminants that may be of more significant concern are those that risk recovery and/or purity of target entities.

Where used herein, "removing contaminants from the sample" refers to the reduction or elimination of contaminants that may be present within a sample. Removing contaminants from the sample may also be referred to as clearing the sample of contaminants and the resulting sample may be referred to as the cleared sample. Removing contaminants from the sample may be accomplished by any appropriate approach, whether or not it is known at the time of this disclosure. By way of non-limiting example, removing contaminants from the sample may be accomplished by centrifugation, filtration, sedimentation, chromatography, dialysis, or variations on any of the foregoing.

In some embodiments, the contaminants may tend to be relatively larger than the target entities. In some embodiments, the contaminants will tend to be relatively smaller than the target entities. In some embodiments. In some embodiments, the contaminants may tend to be both relatively larger and relatively smaller than the target entities. The relative size of the contaminants in the sample, may be defined in terms of their ability to pass through a filter or a chromatography column or to pellet during centrifugation.

In addition to recovering the target entities from a sample, it may be desirable to separately recover some or all of the contaminants included therein. The appropriate time to recover the contaminants is usually dictated by the means used to remove contaminants from the sample. For example, if the target entities are cells then contaminants, such as cell products, may be partitioned into a supernatant, filtrate, or flow-through. Or, if the target entities are extracellular vesicles, such as microvesicles or exosomes, then contaminants, such as cells, may be partitioned into a pellet, residue, or eluate. Or, if the target entities are extracellular vesicles, such as microvesicles or exosomes, then contaminants, such as other cell products (e.g. proteins), may be partitioned into a supernatant, filtrate, or flow-through after the target entities are formed into a complexed population of target entities, as described herein below.

A sample may also include non-target entities, in addition to target entities and contaminants. Non-target entities may be best described as those elements in a sample that would co-localize with the target entities after the contaminants have been removed from the sample, but are not target entities. In some embodiments, non-target entities may belong to the same general class as target entities, but may be distinguished by the absence of the one or more recognition motifs characterizing the target entities. To more clearly illustrate the concept of class, but not intended to limit its breadth, the following examples are provided. In embodiments where the target entities are CD3+ T-cells then non-target entities may be CD3− T-cells or other (CD3−) hematopoietic cells. Or, in embodiments where the target entities are CD9+ extracellular vesicles then non-target entities may be CD9− extracellular vesicles. Or, in embodiments where the target entities are CpG methylated regions of DNA then non-target entities may be unmethylated regions of DNA. Thus, to be considered within the same class the target entities and non-target entities should belong to the same family of biological molecule, structure, or entity.

Where used herein, "binding compositions" refers to those objects capable of a specific binding interaction with the target entities in a sample, and more particularly a specific binding interaction with one or more recognition motifs presented by the target entities. Each binding composition includes at least one moiety capable of interacting with a recognition motif of the target entities. In one embodiment a binding composition includes first and second moieties capable of interacting with a recognition motif of the target entities. In some embodiments a binding composition includes both: (i) a binding composition of first and second moieties each capable of interacting with a recognition motif of the target entities; and (ii) a binding composition of first and second moieties wherein only one of the first and second moieties is capable of interacting with a recognition motif of the target entities. In one embodiment the first and/or second moieties are antibodies or fragments thereof. In one embodiment the first and/or second moieties are aptamers. In one embodiment the first and/or second binding moieties are lectins. Collectively, the plurality of binding compositions may be used to complex a population of target entities.

Where used herein, "recognition motif" refers to a feature present on a surface of the target entities which may be bound by some or all of the plurality of binding compositions. The nature of the recognition motif depends on the nature of the target entity. In embodiments where the target entities are cells or extracellular vesicles, such as microvesicles or exosomes, then the recognition motif may be a protein or glycoprotein present on a surface thereof. In embodiments where the target entities are proteins or peptides then the recognition motif may be an exposed epitope thereof. In embodiments where the target entities are proteins or nucleic acids then the recognition motif may be a sequence feature or a conformation thereof.

Where used herein, "a complexed population of target entities" refers to the target entities naturally present in a sample which are aggregated to one another into a complex on the basis of a specific interaction between one or more recognition motifs thereof and a plurality of binding compositions. Thus, the complexing of target entities does not rely on physical components such as particles—whether magnetic, buoyant, dense, or otherwise—added to the sample, with the exception of the plurality of binding compositions. A complexed population of target entities may be either homotypic or heterotypic.

A homotypic complexed population of target entities will include only members belonging to the same class (as described above) and presenting one or more recognition motifs on a surface thereof capable of interacting specifically with the plurality of binding compositions. Non-limiting examples of a homotypic complexed population of target entities may be an aggregation of: CD9+ extracellular vesicles, such as microvesicles or exosomes; CD4+ T-cells; a specific type of cytokine; RNA molecules encoding a specific, for example, 10-mer sequence; etc.

A heterotypic complexed population of target entities should also include only members belonging to the same class but certain members may present different one or more recognition motifs on a surface thereof capable of interacting with a different plurality of binding compositions. Non-limiting examples of a heterotypic complexed population of target entities may be an aggregation of: CD3+ T cells and CD56+ NK cells; CD9+ extracellular vesicles, such as microvesicles or exosomes, and HSP70+ extracellular vesicles, such as microvesicles or exosomes; two different cytokines; two different miRNAs; etc. For clarity, if cells are the target entities then in the context of this disclosure erythrocytes are not considered to be of the same class, and thus complexing target entities to erythrocytes using erythrocyte:target entity binding compositions is not subject-matter that is encompassed by this disclosure, which is the subject of U.S. Pat. No. 6,448,075.

Methods

In one aspect of this disclosure are provided methods of recovering a population of target entities from a sample.

In one embodiment, the methods disclosed herein may comprise the following steps:

a) removing contaminants from the sample, wherein said contaminants are relatively larger or more dense and/or relatively smaller or less dense than the target entities;
b) contacting the sample of step a) with a plurality of binding compositions, each binding composition having first and/or second moieties capable of binding a recognition motif of the target entities under conditions to allow complexing of the target entities with the plurality of binding compositions to form a complexed population of target entities, the complexed population of target entities having an altered physical property in comparison to the target-entities in individual form; and
c) recovering the complexed population of target entities.

In one embodiment, the methods disclosed herein may comprise the following steps:

a) removing contaminants from the sample, wherein said contaminants are relatively larger or more dense and/or relatively smaller or less dense than the target entities;
b) contacting the sample of step a) with a plurality of binding compositions, each binding composition having first and/or second moieties capable of binding a recognition motif of the target entities under conditions to allow complexing of the target entities with the plurality of binding compositions to form a complexed population of target entities, the complexed population of target entities having an altered physical property in comparison to the target-entities in individual form;

c) fractionating the complexed population of target entities from non-target entities; and d) recovering the complexed population of target entities.

The skilled person will appreciate that the population of target entities may correspond to anything that could be recovered from a sample on the basis of a specific interaction between moieties of a binding composition and a recognition motif of the target entities. Such recovery performed without reliance on supplementing the sample with physical components such as particles—whether magnetic, buoyant, dense, or otherwise—with the exception of the plurality of binding compositions In some embodiments the population of target entities are cells, or a specific population of cells. In some embodiments the population of target entities are cell products, such as biological macromolecules like proteins or nucleic acids, or a specific population of proteins or nucleic acids. In preferred embodiments, the population of target entities are extracellular vesicles, such as microvesicles or exosomes, or a specific population of microvesicles or exosomes.

Depending on the nature of the target entities to be recovered, removing contaminants from the sample may be important for recovering target entities in accordance with the methods disclosed herein. Indeed, the presence of contaminants in a sample may interfere with downstream method steps, and may ultimately result in reduced recovery and/or purity of the target entities. One exemplary embodiment wherein a removal step may be particularly beneficial is where the target entities are extracellular vesicles, such as microvesicles or exosomes, and the sample is a biological sample comprising the target entities and contaminants, such as live or dead cells. In such an embodiment, the live or dead cells may express the same recognition motif as do target entities, in which case the population of target entities would be complexed together with the contaminants, unless the live or dead cells are reduced or eliminated by prior removal of contaminants from the sample.

The removal of contaminants from sample may be by any means, provided that all or substantially all of the target entities are retained therein. Conventional means of removal of contaminants from the sample may include but are not limited to centrifugation, filtration, sedimentation, chromatography, or dialysis. Variations on or combinations of any of the foregoing may also be used to clear the sample.

The means used to clear the sample should be chosen with consideration of the nature of the target entities to be recovered. For example, if removing contaminants from the sample by centrifugation, the rotational speed or gravitational force along with the duration of centrifugation may be important factors. In an embodiment where the target entities are extracellular vesicles, such as microvesicles or exosomes, the sample may be removed of cells and relatively larger debris by centrifugation using a bench top centrifuge at relatively lower centrifugal force so as not to rupture the cells and further contaminate the sample. Where centrifugation is used for removal of contaminants from sample it may be desirable to perform one or more centrifugation steps. Step-wise centrifugation may be used to clear progressively smaller/lighter/less dense contaminants. However, the use of high-speed/force, such as with an ultracentrifuge, to achieve a higher purity of target entities in the cleared sample may come at the cost of reduced yield or recovery. If, by way of additional example, the removal of contaminants from the sample is by filtration, the pore or mesh size should be carefully selected so as not to preclude the recovery of target entities or to unnecessarily include certain contaminants.

While it may be preferred to clear the sample entirely of contaminants, this may not be possible or necessary in all cases. Indeed, an imperfectly cleared sample (e.g. most or substantially all contaminants have been removed) may nonetheless be useful for downstream processes. For example, if contaminants relatively larger than the target entities are cleared from a sample, than relatively smaller contaminants not presenting the one or more recognition motifs would not impact on recovery or purity of the target entities. Nevertheless, whether or not the sample is cleared perfectly or imperfectly, removal of contaminants from the sample will typically facilitate downstream steps of the methods disclosed herein and/or result in improved purity or recovery of target entities.

In many cases it may not be possible to remove all contaminants in an efficient way. If the target entities have a certain size/weight/density and are subjected to centrifugation in order to clear the sample of contaminants, those contaminants having a relatively smaller size/weight/density will remain in the supernatant while those contaminants having a similar or greater size/weight/density as the target entities should also form part of the pellet. In addition, some contaminants having a relatively smaller size/weight/density compared to the target entities may nevertheless become entrained in the pellet. For example, if the target entities are cells or certain types of cells present in a sample of cells and contaminants, such as cell debris (e.g. organelles, cytoskeleton, vesicles, macromolecules, etc.), then the cells and relatively more large/heavy/dense contaminants such as nuclei and cytoskeletal components may co-sediment.

Likewise, if the target entities comprised in a sample have a relatively smaller size/weight/density, it may be readily possible to separate these from contaminants having a relatively larger size/weight/density, such as by centrifugation or filtration, for example. However, it may still be the case that the supernatant or filtrate/flow-through would contain both the target entities and various contaminants. For example, if the target entities are extracellular vesicles, such as microvesicles or exosomes, present in a sample of extracellular vesicles and contaminants, such as cells and cell debris (e.g. organelles, cytoskeleton, vesicles, macromolecules, etc.), than certain cell debris such as macromolecules and certain organelles may co-locate with the extracellular vesicles, such as microvesicles or exosomes.

Even if the sample may be entirely cleared of contaminants, the methods disclosed herein may nonetheless be used to facilitate the recovery of target entities. For example, the methods (and devices) disclosed herein may be used to concentrate the target entities present in a dilute sample.

While the skilled person may otherwise employ significant labour and/or time and/or expense to recover the target entities from a diluted sample, the methods disclosed herein may greatly expedite such undertaking using standard laboratory equipment. In addition, a sample entirely cleared of contaminants may nonetheless include non-target entities, in which case the methods disclosed herein may be used to fractionate the target entities from the non-target entities.

Overall, the approach to removing contaminants from the sample will depend on the nature of the target entities to be recovered. Also, care must be taken to avoid reducing the level of contaminants to such a degree that the recovery of target entities becomes compromised. Thus, in some cases it may be necessary to perform clearing operations in sequence and/or to adopt more than one approach to clearing a sample of contaminants. Regardless, once a sample is cleared of contaminants or cleared of substantially all contaminants, the cleared sample may be subjected to downstream manipulation(s) to recover the target entities, as described below.

Complexing the target entities is carried out by contacting a sample that has contaminants removed (or substantially removed) with a plurality of binding compositions to form a complexed population of target entities. The plurality of binding compositions will be capable of bridging first and second target entities in the sample. Thus, some or all of the plurality of binding composition may comprise first and/or second moieties capable of binding a recognition motif of the target entities. In such fashion, it is apparent how multiple target entities may be held together in a complex through the combined operation of the plurality of binding compositions by bridging one target entity to another, and so on.

The plurality of binding compositions, and more specifically the first and second moieties thereof, can take any form, provided they are capable of specifically binding a recognition motif presented by a target entity. In one embodiment, the first and second moieties may be antibodies, or fragments thereof. In one embodiment, the first and second moieties may be aptamers, such as oligonucleotide or peptide molecules. In one embodiment, the first and second moieties may be lectins.

The first and second moieties of the plurality of binding compositions may be linked directly or indirectly. In one embodiment, the first and second moieties are directly (covalently) conjugated to each other. In some embodiments, the linkage of first and second moieties is effected by one or more intermediaries. For example, first and second moieties may be conjugated to a common polymer or common bead or particle. In a specific embodiment, the first and second moieties may be held together (i.e. linked) by third and fourth moieties. In some embodiments, the first and second moieties may be antibodies, or fragments thereof, raised in a first species and the third and fourth moieties may be anti-isotype antibodies, or fragments thereof raised in a second species. In such embodiments, the configuration of first, second, third, and fourth antibodies or fragments thereof may be referred to as a tetrameric antibody complex, as described elsewhere (U.S. Pat. No. 4,868,109).

The first and second moieties may bind to the same or different recognition motif. If a binding composition comprises first and second moieties that binds to the same type of recognition motif, it may be characterized as a mono-specific binding composition and the resulting complexed population of target entities may be characterized as homotypic. However, if a binding composition comprises first and second moieties that bind to different recognition motifs, it may be characterized as a bi-specific binding composition and the resulting complexed population of target entities may be characterized as heterotypic. If a binding composition comprises more than two moieties that bind to a recognition motif, it may be characterized as a multi-specific binding composition and the resulting complexed population of target entities may be characterized as heterotypic.

To expand on the foregoing, in one embodiment a sample may comprise target entities that are extracellular vesicles, such as microvesicles or exosomes. Extracellular vesicles, such as microvesicles or exosomes, may present either CD9 or CD63 or CD81 recognition motifs, or any combination of the foregoing. In some embodiments, the make-up of the plurality of binding compositions may be selected based on the type of extracellular vesicle(s) to be recovered. For example, CD9+ extracellular vesicles may be the target entities intended to be recovered from a sample, in which case the first and/or second moieties of the plurality of binding compositions may be anti-CD9 antibodies, or fragments thereof. Thus, the CD9+ extracellular vesicles in the sample may form a complexed population of target entities with the plurality of binding compositions bridging first and second target entities. Such a complexed population of target entities could be considered homotypic.

In the foregoing example, if CD9− extracellular vesicles, such as microvesicles or exosomes, are also present in the sample, they would be considered non-target entities. After the CD9+ extracellular vesicles are formed into a complexed population (and recovered), the non-target entities may then be recovered, whether specifically (through the use of a second plurality of binding compositions) or in bulk.

In one embodiment the target entities may be both CD9+ and CD63+ extracellular vesicles. In such case, the make-up of the selected binding compositions may depend on whether some or all of the target entities co-express these markers. If so, forming the complexed population of target entities may be achieved using mono-specific binding compositions (e.g. anti-CD9:anti-CD9 and anti-CD63:anti-CD63) or bi-specific binding compositions (e.g. anti-CD9:anti-CD63), or both mono- and bi-specific binding compositions (e.g. anti-CD9:anti-CD9, anti-CD9:anti-CD63, anti-CD63:anti-CD63). Such a complexed population of target entities may also be considered homotypic.

If the markers are not co-expressed and it is desired to form a single complexed population of target entities, than it will be necessary to contact the sample (that has contaminants removed) with at least some bi-specific binding compositions. Such a complexed population of target entities may also be considered homotypic on the basis that all the target entities are either cells or extracellular vesicles, such as microvesicles or exosomes.

In one embodiment the target entities may be cells, such as CD3+ cells, present in a sample such as a blood sample. (If the sample is a blood sample or the like, it may be desirable to treat red blood cells as among the contaminants for removing, which will be within the ability of the person skilled in the art by various commercial and classical means). In such case, the first and second moieties of the plurality of binding compositions may be anti-CD3 antibodies, or fragments thereof. Thus, the CD3+ cells in the sample may form a complexed population of target entities as a binding composition bridges first and second target entities, and so on for all (or most) CD3+ cells in the sample.

According to the logic described above, it may be possible to form a complexed population of target entities presenting any number of different recognition motifs, provided that the character of the binding compositions is appropriately considered. As indicated above, it may be possible to include pluralities of one, two, three, or more different binding compositions. By way of example, if all of CD9+, CD63+, and CD81+ extracellular vesicles, such as microvesicles or exosomes, are desired for recovery from a sample, then depending on the co-expression or the absence of co-expression of these markers at least three different pluralities of binding compositions should be used to contact the sample from which contaminants were removed.

The plurality of binding compositions may be pre-formed or assembled in the sample (i.e. in situ). In most cases, it may be preferable to pre-form the plurality of binding compositions, such as when forming the plurality of binding compositions involves reaction conditions not tolerated by the target entities in the sample. For example, the chemical conjugation of antibodies whether to each other or to a polymer or particle/bead would be harmful to most types of target entities. However, in other cases it may be possible and/or preferable to form the binding compositions in the sample itself and/or on the target entities therein in situ.

In embodiments where the first and second moieties of the binding compositions are held together by third and fourth binding moieties, so as to form an immunological complex, such binding compositions may be formed either in advance or in the sample. On the one hand, such binding compositions may be pre-formed by combining the appropriate molar concentrations of first and second moieties and third and fourth moieties followed by incubation at room temperature or thereabout for a time sufficient to allow the immunological complexes to self-assemble. On the other hand, such binding compositions may be formed in the sample by adding thereto the first and second moieties and the third and fourth moieties, whether step-wise or all at once, followed by incubation at room temperature or thereabout for a time sufficient to allow the immunological complexes to self-assemble. The self-assembly process may take about 5 minutes, 10 minutes, 15 minutes, 20 minutes, 30 minutes, 40 minutes, 50 minutes, 60 minutes, or more.

The concentration, or more appropriately the number, of binding compositions used to contact a sample may be an important consideration in the disclosed methods for recovering target entities from a sample. If too many binding compositions are used to contact the sample, then the efficiency of complexing the target entities may be reduced. In an extreme example, if a sufficient number of binding compositions are used to contact the sample such that each recognition motif of the target entities is saturated, then there are likely to be few if any instances where the binding compositions bridge first and second target entities, and thus little to no complexing of the target entities will occur. This result is likely independent of whether or not mono, bi-, or multi-specific binding compositions are used. Therefore, it is preferable that the plurality of binding compositions are at below-saturation levels. Under ideal conditions, the number of binding compositions comprising first and second moieties used to contact the sample should be half of the number of recognition motifs present therein. However, if too few binding compositions are used to contact the sample, then the risk may be of reduced, if any, recovery of target entities within a recovered complexed population of target entities.

Upon contacting the sample from which contaminants have been removed with a plurality of binding compositions, a complex of target entities would be formed in accordance with the complexing conditions. In some embodiments, a complex of target entities may form in a matter of minutes, such as in about 1 minute, or in about 2 minutes, or in about 3 minutes, or in about 5 minutes, or more. In some embodiments, a complex of target entities may form in tens of minutes, such as in about 10 minutes, or in about 20 minutes, or in about 30 minutes, or in about 50 minutes, or more. In some embodiments, a complex of target entities may more in hours or overnight. Nevertheless, a longer incubation period may increase the potention for non-specific interactions, thereby reducing purity. For example, if the complexing takes place at colder temperatures, such as at about 4° C., then the reaction may require an hours long incubation. Thus, shorter duration incubations may be preferable, in which case the incubation may take place at relatively less cold temperatures, such as at about room temperature or at 37 C or higher.

In some embodiments where the target entities are extracellular vesicles such as microvesilces or exosomes, a complex thereof may form in 5 minutes or less. In some embodiments where the target entities are extracellular vesicles such as microvesicles or exosomes, a complex thereof may be allowed to form overnight without apparent effects on the physical properties of the complex or on the stability of the target entities.

Once a complexed population of target entities is formed such target entities may be recovered by any known means. The complexed population of target entities may be readily recovered by means such as centrifugation, filtration, chromatography, etc. Since the complexing has changed one or more physical properties of individual target entities, the complexed population of target entities may be recovered on the basis of the altered one or more physical properties. For example, a complexed population of target entities may have a larger dimension, weight and/or density then do individual (un-complexed) target entities. After a recovery operation, the recovered complexed population of target entities—whether in the form of a pellet, residue, or eluate—may be resuspended or diluted as appropriate for downstream applications.

In embodiments where the complexed population of target entities is separable from contaminants on the basis of size, it may be necessary to pre-clear the sample of any entities having a roughly equal size as would a complex of target entities. Thus, the contaminants may be first cleared by filtration, centrifugation, chromatography, then the target entities may be complexed to change their physical properties, thereby enabling their separation from the pre-cleared sample, where they could not be readily separated by conventional and time-efficient techniques but for altering their physical properties.

In one specific embodiment, extracellular vesicles, such as microvesicles or exosomes, are intended to be recovered from a biological sample, such as blood, bone marrow, a tissue homogenate, urine, or a cell culture medium, whether or not conditioned by the culture of cells. In such an embodiment, the extracellular vesicles, such as microvesicles or exosomes, may present CD9 and/or CD63 and/or CD81 recognition motifs, and the extracellular vesicles, such as microvesicles or exosomes, of interest are complexed on the basis of an interaction between the recognition motifs and moieties of a plurality of binding compositions (e.g. anti-CD9 and/or anti-C63 and/or anti-CD81 antibodies or fragments thereof), as described herein. Such complexed population of target entities may be recovered by, for example, centrifugation or filtration.

Optionally, it may also be desirable to recover non-target entities and/or contaminants from the cleared sample (in addition to the complexed population of target entities). Given the altered physical property of a complexed population of target entities as compared to individual target entities, such as on the basis of size or density, the act of recovering the complex may simultaneously fraction the cleared sample into, for example, a pellet or residue comprising the target entities and a supernatant or filtrate comprising non-target entities and/or contaminants. Thus, fractionating the complexed population of target entities from non-target entities and/or contaminants may be an unavoidable by-product of recovering the complexed population of target entities. In any event, the non-target entities and/or contaminants may have biological value and may be readily recovered and also used in downstream applications.

In one embodiment, a complexed population of CD9+ extracellular vesicles, such as microvesicles or exosomes, may be recovered from a cleared sample by, for example, centrifugation or filtration. In such an embodiment, pelleting or filtering the complexed population of target entities may yield a supernatant or filtrate comprising extracellular vesicles, such as microvesicles or exosomes, that do not present CD9 recognition motifs. Such CD9− extracellular vesicles may be recovered from the cleared and fractionated sample. It may also be desirable to recover other contaminants such as organelles, cytokines, macromolecules, etc. from such a cleared sample.

In one embodiment, a complexed population of CD3+ cells may be recovered from a cleared sample by, for example, centrifugation or filtration yielding a supernatant or filtrate of CD3− negative cells and possibly other contaminants. If, for example, it is desirable to subsequently recover CD56+ cells (and to keep such cells separate from the complexed population of CD3+ cells) then the supernatant or filtrate may be processed accordingly.

After fractionating, the sample from which the complexed population of target entities have been recovered may require further manipulation to recover the non-target entities and/or contaminants of interest. As with clearing the sample in the first place or recovering the complexed population of target entities, the non-target entities and/or contaminants included in the cleared (and fractionated) sample may be recovered on the basis of size/weight/density, such as by centrifugation, filtration, chromatography, dialysis, etc. Nevertheless, the type of manipulation will depend on the nature of non-target entities and/or contaminants of interest. Indeed, if a specific population of non-target entities and/or contaminants are intended to be recovered, then a plurality of binding compositions including appropriate first and second moieties may be utilized. If bulk populations of non-target entities and/or contaminants are intended to be recovered, more general approaches may be more appropriate. For example, if the non-target entities or contaminants are nucleic acids, then the fractionated sample may be subjected to processing by any known method, such as by phenol:chloroform extraction or using a silica-based column, each of which exploit centrifugation. In other cases, for example, the non-target entities or contaminants may be recovered by centrifugation or filtration. Whatever the nature of the non-target entities and/or contaminants of interest, the skilled person will be able to find a commercial means or adapt the subject-matter disclosed herein to facilitate the recovery thereof.

The methods of this disclosure, or any step thereof, may be carried out in any appropriate container or vessel. In a preferred embodiment, the methods or any step thereof may be carried out using standard glass or plastic centrifuge tubes, such as 50 mL, 15 mL, 5 mL, or 1.5 mL tubes. In another embodiment, the methods may be carried out using a device in accordance with the disclosure below.

Devices

In another aspect of this disclosure are provided devices for recovering a population of target entities from a sample. Use of such devices implement, essentially, the methods disclosed herein.

Device 1 (as shown in FIGS. 1 to 4) may comprise a first porous unit 10 and a second porous unit 100. Second porous unit 100 may be positioned downstream of, relative to a flow path 5 of a sample, and in fluid communication with first porous unit 10. Device 1 may also comprise a chamber 50 between first porous unit 10 and second porous unit 100, and said chamber 50 may include therein a plurality of binding compositions, as described elsewhere herein.

In one embodiment, first porous unit 10 comprises a first pored member 15 flanked by first inlet 20 and first outlet 25. First inlet 20 may take any form provided that it is capable of receiving sample therethrough. First inlet 20 may comprise first end 22 which may be connectable to a syringe, pipette tip, tubing, etc. In one embodiment, first end 22 may be threaded, such as a Luer lock. In one embodiment, first end 22 may be tapered and/or comprise one or more annular ridges on an outer surface thereof.

A pore size of first pored member 15 may be selected based on transmissibility of desired target entities. Thus, first porous unit 10 may be impervious to contaminants relatively larger than the target entities. If on the one hand the target entities are specific mammalian cells, such as CD3+ T cells, a pore size of about 30 μm will permit most (mammalian cell types) to pass therethrough, while preventing the flow through of larger contaminants such as cell aggregates or fragments of tissues. If on the other hand the target entities are extracellular vesicles, such as microvesicles or exosomes, such as CD9+ exosomes, a pore size of about 1 μm may permit certain organelles, certain vesicles, such as extracellular vesicles or exosomes including the CD9+ exosomes, and macromolecules to flow through, while preventing the flow through of larger contaminants such as tissue fragments, cell aggregates, cells, certain organelles such as nuclei, and certain larger vesicles.

In some embodiments, first pored member 15 may also be of a size that is impervious to one or more complexed populations of target entities. In some embodiments, a pressure may be applied or maintained upstream of first porous unit 10 to prevent the back-flow through first outlet 25 toward first inlet 20.

Similar to first inlet 20, first outlet 25 may also take any form provided it is a capable conduit of filtrate to a downstream porous unit, either directly or indirectly via chamber 50. In one embodiment, first outlet 25 may comprise second end 27, and second end 27 may be connectable to a downstream porous unit or chamber 50. In one embodiment, second end 27 may be threaded, such as a Luer lock. In one embodiment, second end 27 may be tapered and/or comprise one or more annular ridges on an outer surface thereof. In one embodiment, first outlet 25 may comprise no end and filtrate having passed through first pored member 15 may empty directly into chamber 50.

Second porous unit 100 comprises a second pored member 105 flanked by second inlet 120 and second outlet 125. Second inlet 120 may take any form provided that it is capable of receiving filtrate therethrough. Second inlet 120 may comprise third end 122, and third end 122 may be connectable to first porous unit 10 (more specifically to second end 22) or to chamber 50. In one embodiment, third end 122 may be threaded, such as a Luer lock. In one embodiment, third end 122 may be tapered and/or comprise one or more annular ridges on an outer surface thereof. In one embodiment, second inlet 120 may comprise no end and filtrate having passed through first porous unit 10 and/or chamber 50 may be received directly from chamber 50.

A pore size of second pored member 105 may be selected based on imperviousness of the complexed population of target entities, while being transmissible to other relatively smaller contaminants having passed through first porous unit 10 to also pass through second porous unit 100. If on the one hand the target entities are mammalian cells, such as CD3+ T cells, and such cells form a complexed population of target entities in chamber 50, then the pore size of second pored member 105 is flexible. For example, if the complexed population of target entities approaches a diameter of about 100 μm- to 1 mm or more, the pore size of second pored member 105 may be anything smaller than the expected diameter of the complexed population of target entities. If on the other hand the target entities are extracellular vesicles, such as microvesicles or exosomes, such as CD9+ exosomes, and such extracellular vesicles form a complexed population of target entities in chamber 50, then the pore size of second pored member 105 should be carefully chosen. For example, if the complexed population of target entities approaches a diameter of about 0.5 μm to 1 urn or more, the pore size of the second pored member 105 may be anything smaller than the expected diameter of the complexed population of target entities.

As with first inlet 20, second outlet 125 may also take any form provided it is a capable conduit of filtrate for disposal or further downstream processing. Second outlet 125 may comprise fourth end 127, and fourth end 127 may be connectable to a discharge receptacle. In one embodiment, fourth end 127 may be threaded, such as a Luer lock. In one embodiment, fourth end 127 may be tapered and/or comprise one or more annular ridges on an outer surface thereof. In one embodiment, second outlet 125 may comprise no end and filtrate having passed through second porous unit 100 may be discharged out of device 1 into the environment or an appropriate container.

Figure 3:
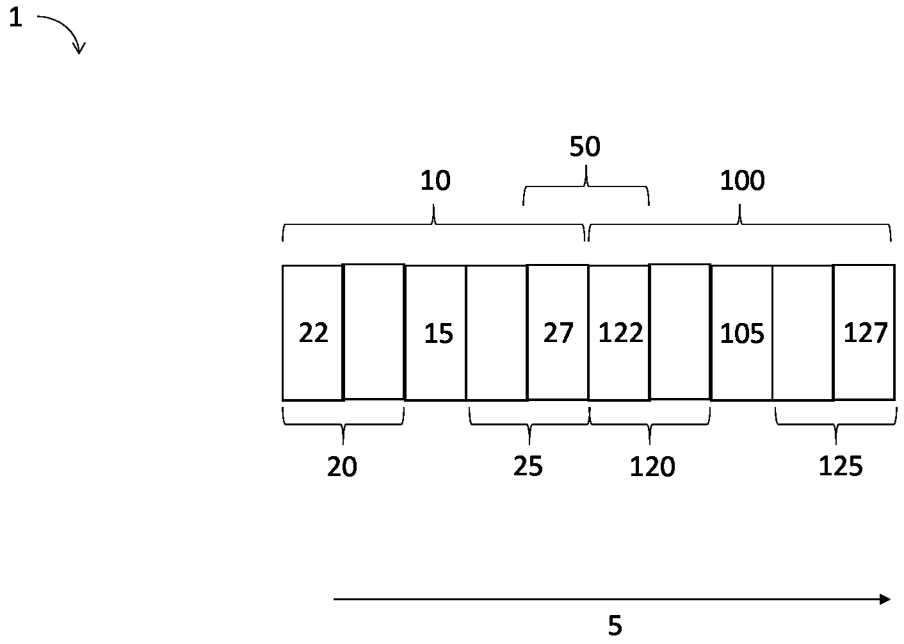
FIG. 3 shows a diagram of one embodiment of a device for recovering a population of target entities from a sample.

In certain cases, such as when the target entities are particularly small, such as extracellular vesicles or exosomes (e.g. 50-200 nm in diameter), then it may be desirable to include in series more than one porous unit upstream of chamber 50 to achieve better fluid dynamics efficiencies, such as reduced clogging of porous units (FIG. 3). Such plurality of upstream porous units may have successively smaller pore sizes. For example, if the target entities are extracellular vesicles, such as microvesicles or exosomes, such as CD9+ exosomes, first pored member 15 may have a pore size of 30 μm to screen out relatively larger contaminants. A third porous unit 200, immediately downstream of first porous unit 10, may comprise a third pored member 205 (flanked by third inlet 220 having a firth end 222 and a third outlet 225 having sixth end 227) having a relatively smaller pore size than first pored member 15, such as 5 μm, 2 μm, or 1 μm, to screen out contaminants that pass through the first porous unit 10 while still enabling the target entities to flow into chamber 50. Likewise, it may be desirable to include additional porous units downstream of chamber 50, in order to fractionate components other than target entities within the sample.

Figure 2:
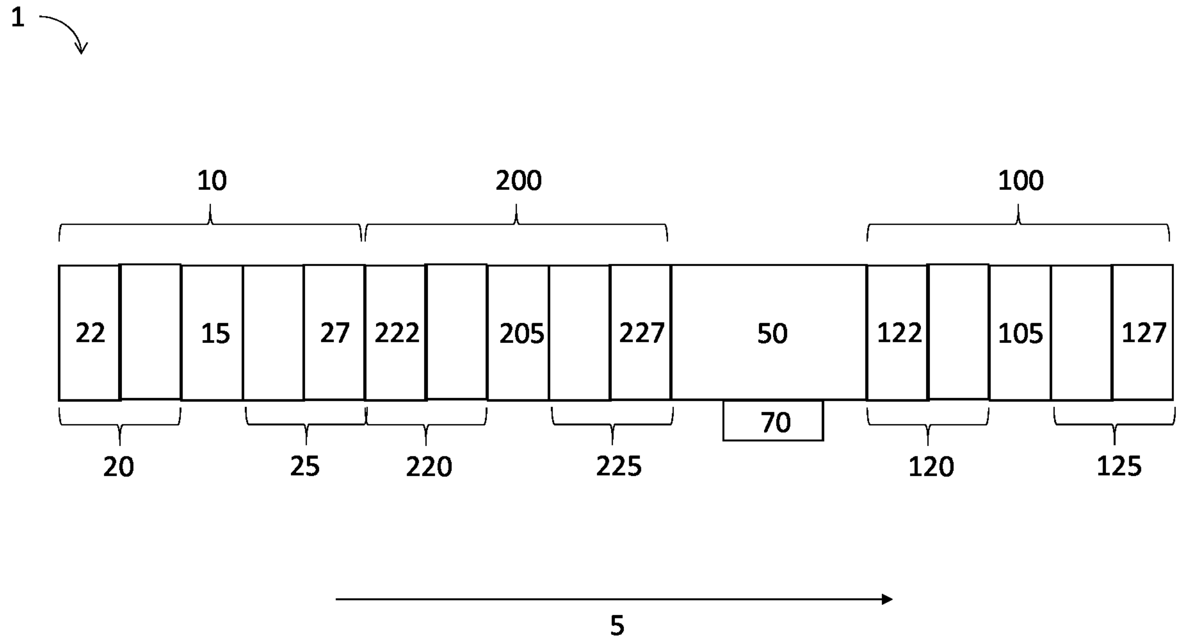
FIG. 2 shows a diagram of one embodiment of a device for recovering a population of target entities from a sample.
Figure 4:
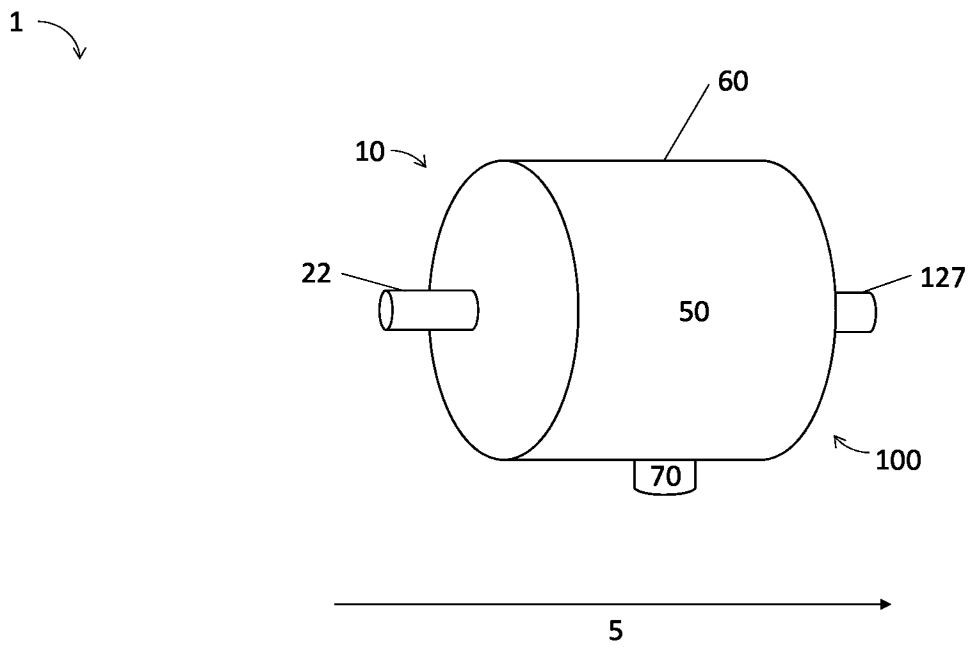
FIG. 4 shows a perspective view of one embodiment of a device for recovering a population of target entities from a sample.

Chamber 50 may take any form provided that it can receive filtrate from an upstream porous unit and hold received filtrate therein. The chamber 50 should be capable of holding most or all of the sample (more accurately the filtrate) received therein. In one embodiment, chamber 50 is formed upon connecting second end 27 of first porous unit 10 and third end 122 of second porous unit 100 (FIG. 3, which may also include outlet means 70; not shown). In one embodiment, chamber 50 may be a modular unit connectable to second end 27 of first porous unit 10 and third end 122 of second porous unit 100 (FIG. 1) or connectable to sixth end 227 of third porous unit 200 and third end 122 of second porous unit 100 (FIG. 2). In one embodiment, chamber 50 may be formed by housing 60 that encloses first outlet 25 and second inlet 125 (FIG. 4).

Chamber 50 may hold a plurality of binding compositions (as described above) therein. The plurality of binding compositions may be pre-loaded into chamber 50, or they may be loadable therein by a user. In one embodiment, the plurality of binding compositions within chamber 50 (whether pre-loaded or not) are in aqueous phase. In one embodiment, the plurality of binding compositions within chamber 50 (whether pre-loaded or not) are lyophilized, which become reconstituted (i.e. rehydrated) upon coming into contact with the filtrate received in chamber 50. A lyophilized plurality of binding compositions may reduce expenses associated with shipping, storage, and shelf-life.

Once the plurality of binding compositions come into contact with the filtrate in chamber 50, the target entities may become complexed. The formation of a complexed population of target entities within chamber 50 preferably requires incubating the target entities and the plurality of binding compositions for a sufficient duration of time. In some embodiment, the incubation may be about 5 minutes, 10 minutes, 15 minutes, 20 minutes, 30 minutes, 40 minutes, 50 minutes, 60 minutes, or more. A longer incubation time may be necessary when the plurality of binding compositions are lyophilized rather than in aqueous phase.

The complexed population of target entities may be recovered from chamber 50 through outlet means 70. Outlet means 70 may take any form provided that it is a capable conduit of the complexed population of target entities. In one embodiment, outlet means may be a valve or a spigot connectable to a pipette tip, a syringe, or tubing. In one embodiment, outlet means may be a puncturable membrane such as by a pipette tip or a syringe.

Once the complexed population of target entities is formed, it may be desirable to evacuate the filtrate from chamber 50 through a downstream porous unit. Evacuating the chamber may be desirable to drive contaminants to fractionate the complexed population target entities from contaminants that may be present in the filtrate. It may also be desirable to wash the complexed population of target entities by urging a suitable buffer, such as PBS, through first pored member 15 into chamber 50 and through second pored member 105. Regardless of whether or not the complexed population of target entities is fractionated from contaminants in the filtrate or washed, it is preferred to recover the target entities from chamber 50 in an aqueous phase, and preferably in a sterile buffer such as PBS.

In operation, a user may load a sample through first porous unit 10 of device 1, such as by connecting a syringe, pipette tip, or tubing to first end 22 of first inlet 20 and deploying the sample through first pored member 15. As the sample passes through first porous unit 10, depending on the pore size, various contaminants may be removed from the sample as it traverses first pored member 15. The filtrate is received into chamber 50 via first outlet 25, wherein the filtrate comes into contact with a plurality of binding compositions contained therein. During an appropriate incubation time the target entities complex via the plurality of binding compositions to form a complexed population of target entities. Thereafter, the filtrate is urged into second porous unit 100 and through second pored member 105, which is impervious to the complexed population of target entities. Thereby, the complexed population of target entities is retained in chamber 50 and fractionated from the filtrate, and the various contaminants, which pass through second pored member 105 and out second outlet 125 for disposal or further downstream processing. The complexed population of target entities may be recovered via outlet means 70. Prior to recovering the complexed population of target entities via outlet means 70, it may be desirable to wash the complexed population of target entities, such as by passing a volume of a wash buffer (e.g. PBS or the like) through first porous unit 10 into chamber 50 and through second porous unit 20.

Sample and filtrate may be moved through device 1 using conventional means. In one embodiment, sample and filtrate may be moved through device 1 by applying positive pressure/force upstream of first porous unit 10. For example, a syringe with a plunger may provide the necessary pressure/force to move the sample through first pored member 15 and the resulting filtrate into chamber 50 and through second pored member 115.

In one embodiment, sample and filtrate may be moved through device 1 by applying negative pressure/force downstream of second porous unit 100. For example, a vacuum apparatus may be connected to second outlet 125 to pull the sample through first member 15 and the resulting filtrate into chamber 50 and through second porous member 115.

In one embodiment the sample may be fully discharged through first pored member 15 into chamber 50, and additional solution, such as PBS, may be urged, whether by positive or negative pressure/force, through first pored member 15 in order to drive the filtrate in chamber 50 through second porous unit 100.

Regardless of whether or not positive or negative pressure is applied to urge a sample and/or filtrate through device 1, it may be desirable that such pressure is constant. In some embodiments, it may be desirable to cease applying the pressure during an incubation phase when the target entities are complexed via the plurality of binding compositions. In some embodiment, it may be desirable to maintain a level of pressure as the target entities are complexing (via the plurality of binding compositions) in chamber 50 so as to prevent a back-flow into and through first porous unit 10.

Using device 1 it may be possible to quantify the number of target entities in a sample. For example, the number of T cells in a blood sample may be used as a proxy for immune system activity, such as in patients that may be suffering an infection. In one embodiment, a 1 mL sample of blood may be urged via first porous unit 10 into chamber 50. After a sufficient incubation period to allow a complexed population of target entities (e.g. CD3+ T cells) to form, the filtrate within chamber 50 may be further urged through second porous unit 100. The volume of filtrate traversing second pored member 115 before it becomes clogged may be used to calculate the number of target entities in the sample.

In one embodiment, it may be important that device 1 is a closed system, so as to maintain the sterility of the sample and/or target entities and/or filtrate.

Porous units and chambers may be differently sized depending on the volume of sample to be processed. Further, porous units and chambers may be pre-assembled or assemblable by the user.

The following non-limiting examples are illustrative of the present disclosure.

EXAMPLES

Example 1: Preparing the Sample

In this example the sample prepared is a cell culture medium conditioned by the culture of mesenchymal stem cells in MesenCult™ culture medium (STEMCELL Technologies) according to standard protocols and human plasma (StemExpress).

The contaminants were removed from the sample by centrifuging the sample at 2000×g for 10 minutes at 4° C. At such level and duration of gravitational force, contaminants such as cells and other bodies having a similar or greater mass/density would pellet while leaving relatively smaller objects suspended in the supernatant. The supernatant was subsequently subjected to centrifugation at 10000×g for 30 minutes either at room temperature or at 4° C. At such level and duration of gravitational force, contaminants such as cellular debris and other bodies of similar size would pellet while leaving relatively smaller objects suspended in the supernatant. The supernatant is ready for further downstream processing.

For certain samples, such as plasma, it may be desirable to filter the supernatant following the 30 minute-long centrifugation, prior to moving on to downstream steps. Usually, it is not necessary to subject samples having low levels of contaminants to such filtration, provided that the sample has been appropriately cleared by some other means, such as chromatography, filtration, or the like. If a filtration step is employed, it is important to select a proper pore size that would permit objects of interest to flow-through. In the case of extracellular vesicles, such as exosomes, a pore size of about 0.2 μm is appropriate.

Samples other than conditioned cell culture medium or plasma, such as urine or blood, may be prepared in essentially the same way as described above.

Example 2: Preparing the Binding Compositions

To assemble a plurality of binding compositions, 30 μg/mL of first and second moieties suspended in an appropriate buffer, such as PBS, were combined with 30 μg/mL of third and fourth moieties suspended in an appropriate buffer, such as PBS. Combined first and second and third and fourth moieties were incubated at room temperature or 37° C. for 30 minutes to allow the plurality of binding compositions to self-assemble. The incubation may also be done at room temperature overnight.

In this example, the first and second moieties correspond to anti-CD9 antibodies (Biolegend) and the third and fourth moieties correspond to anti-isotype antibodies that hold the CD9 antibodies together in an immunological complex. Immunological complexes of anti-CD63 binding compositions and anti-CD81 binding compositions may be likewise prepared.

The plurality of binding compositions (i.e. anti-CD9 complexes, anti-CD63 complexes, and anti-CD81 complexes) may be intended for use either individually or in combination. Regardless of whether or not the plurality of binding compositions are used individually or in combination, their final concentration should be 30 μg/mL.

Example 3: Complexing Target Entities

In order to complex a population of target entities in the sample, the sample prepared in accordance with Example 1 was contacted with the plurality of binding compositions prepared in accordance with Example 2.

Briefly, 1 mL of sample prepared as described in Example 1 was pipetted into a 1.5 mL centrifuge tube and was contacted with 100 μL of 30 μg/mL binding compositions, prepared as described in Example 2. If it is desirable to process more than 1 mL of prepared sample, than a corresponding increase in prepared binding compositions may be necessary (i.e. 100 μL binding compositions per 1 mL of prepared sample). Once the prepared sample is contacted with the prepared binding compositions, the complexing reaction is incubated at room temperature for about 30 minutes.

In this example, the target entities are the population of CD9+, CD63+, or CD81+ extracellular vesicles, such as microvesicles or exosomes, when using respectively anti- CD9 binding compositions, anti-CD63 binding compositions, and anti-CD81 binding compositions for complexing. Also in this example, the target entities are the population of microvesicles or exosomes that are complexed when the sample is contacted with each of anti-CD9 binding compositions, anti-CD63 binding compositions, and anti-CD81 binding compositions (the "pan-conditions").

Example 4: Recovering the Complexed Target Entities

After the complexed population of target entities is formed, the target entities are recovered, such as by centrifugation, filtration, chromatography, or the like.

In this example, the formed complexes are recovered by centrifugation at 17000×g in a standard benchtop centrifuge for 20 minutes at room temperature. The supernatant may be stored for further processing, such as to recover bodies that would not have been bound by the binding compositions, whether contaminants (e.g. cytokines or other proteins) or non-target entities (e.g. exosomes that do not express the recognition motifs). The pellet may be resuspended in an appropriate buffer, such as PBS, and subjected to downstream applications.

Depending on the nature of the starting sample, the pellet may be washed using 1 mL PBS and recovered by centrifugation at 17000×g in a standard benchtop centrifuge for 20 minutes at room temperature. After removing the supernatant, the pellet may be resuspended using 60 μL PBS and subjected to downstream applications, such as Western blot, ELISA, RNA and/or DNA isolation, etc.

Example 5: Analyzing the Target Entities by Western Blot

To demonstrate the ability of the disclosed methods to recover the desired population of target entities, the recovered complexed population of target entities of Example 4 was subjected to polyacrylamide gel electrophoresis and Western blot. Western blots were performed using standard equipment and standard protocols, except that the recovered target entities were not reduced.

Briefly, 30 μL of target entities recovered in Example 4 were diluted with 10 μL 4× Laemmli buffer (BioRad) and heated to, among other things, lyse the target entities. Approximately 35 μL of the heated solution was loaded per well and run on a 10% poly-acrylamide non-reducing gel. Membranes were probed with CD9-HRP conjugate (0.25 μg/mL), CD81-HRP conjugate (0.25 μg/mL), CD63-HRP conjugate (0.5 μg/mL).

Figure 5:
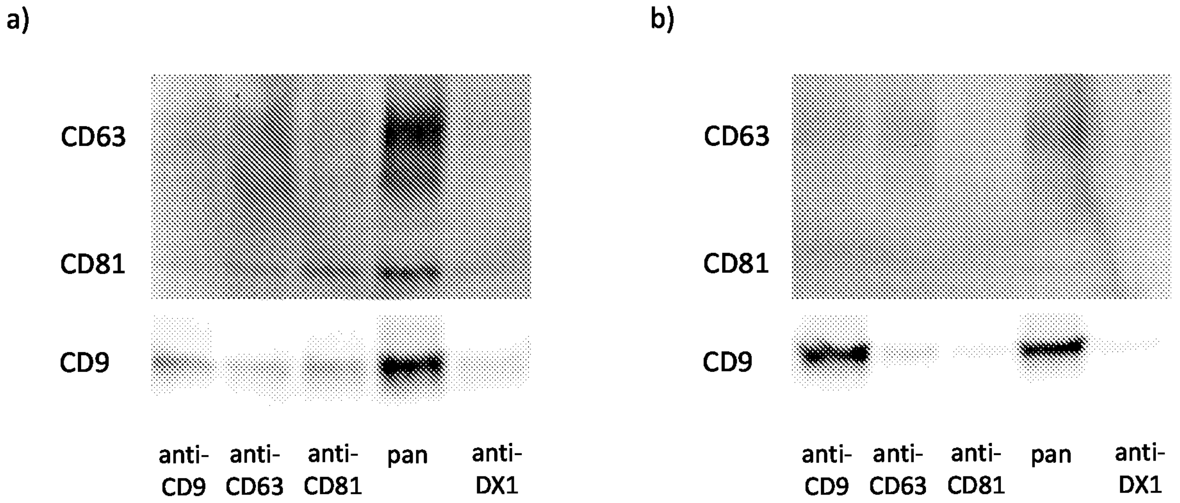
FIG. 5 shows a Western blot of target entities recovered from (a) conditioned cell culture medium and (b) human plasma. The nature of each binding composition used to recover the complexed populations of target entities is indicated beneath each lane, which is also indicative of the specificity of the antibody used to probe the blots.

The results in FIG. 5 show that anti-CD9 binding compositions recovered CD9+ positive extracellular vesicles, such as microvesilces and/or exosomes, and so forth in regard to anti-CD63 and anti-CD81 binding compositions. The results in FIG. 5 also show that at least some of the CD9+ extracellular vesicles and/or exosomes recovered using anti-CD9 binding compositions appear to co-express one or both of CD63 and CD81 recognition motifs, and so forth in regard to the populations of CD63+ and CD81+ extracellular vesicles, such as microvesicles and/or exosomes. The results in FIG. 5 still further show that the pan-condition for recovering microvesicles and/or exosomes appears to yield the highest enrichment.

Example 6: Complexed Populations of Extracellular Vesicles Form Rapidly

In order to complex a population of target entities in the sample, the sample prepared in accordance with Example 1 was contacted with the plurality of binding compositions prepared in accordance with Example 2.

Figure 6:
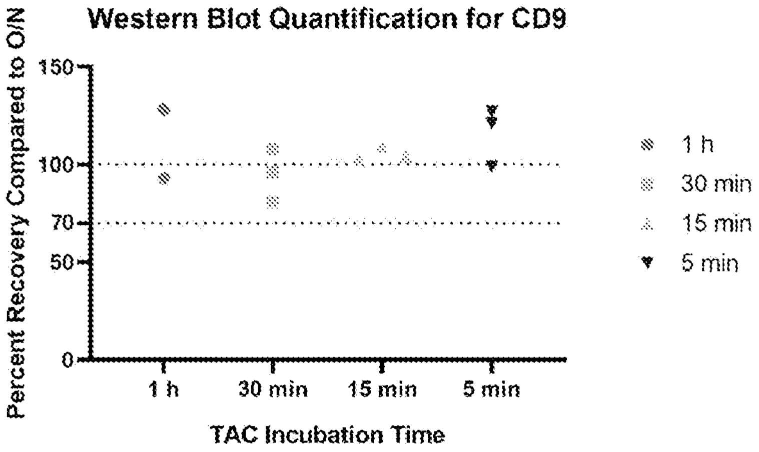
FIG. 6 shows a graph of target entities recovered from conditioned cell medium. Complexing of target entities using a pan-agglutination binding composition was tested over multiple time points.

In FIG. 6 it is shown that complexes of target entities in conditioned cell culture medium may form rapidly. Similar or higher numbers of extracellular vesicles could be recovered when complexes of extracellular vesicles were formed for 5 minutes up to 60 minutes, as compared to complexes of extracellular vesicles formed overnight. Complexes of extracellular vesicles were pelleted by centrifuging for 1 hour at 4° C., and extracellular recovery was compared with western blot densitometry analysis.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

What is claimed:

1. A device for recovering a population of target entities from a sample comprising target entities and contaminants, the device comprising:

a) a first porous unit having a first pored member flanked by a first inlet and a first outlet;

b) a second porous unit having a second pored member flanked by a second inlet and a second outlet, the second porous unit positioned downstream of and in fluid communication with the first porous unit;

c) a chamber between the first porous unit and the second porous unit; and d) a plurality of binding compositions loaded or loadable in the chamber, each binding composition having first and second moieties capable of interacting with a recognition motif of the target entities, wherein (i) the plurality of binding compositions are in aqueous phase, (ii) the plurality of binding compositions complex the target entities to form a complexed population of target entities in the chamber, (iii) a pore size of the second pored member is impervious to the complexed population of target entities, and (iv) the first and second moieties are antibodies or fragments thereof.

2. The device according to claim 1, wherein the pore size of the first pored member is impervious to the complexed population of target entities.

3. The device according to claim 1, wherein the plurality of binding compositions are at below-saturation levels.

4. The device according to claim 1, wherein the first and second moieties interact with the same or different recognition motif.

5. The device according to claim 1, wherein the first and second moieties are conjugated directly to one another or held together by third and fourth moieties, and the third and fourth moieties are antibodies or fragments thereof.

6. The device according to claim 1, wherein the first outlet and the second inlet are connectable thereby forming the chamber.

7. A device for recovering a population of target entities from a sample comprising target entities and contaminants, the device comprising:

a) a first porous unit having a first pored member flanked by a first inlet and a first outlet;

b) a second porous unit having a second pored member flanked by a second inlet and a second outlet, the second porous unit positioned downstream of and in fluid communication with the first porous unit;

c) a chamber between the first porous unit and the second porous unit;

d) an outlet means distinct from the first outlet and the second outlet for recovering target entities from the chamber; and e) a plurality of binding compositions loaded or loadable in the chamber, each binding composition having first and second moieties capable of interacting with a recognition motif of the target entities, wherein (i) the plurality of binding compositions are in aqueous phase, (ii) the plurality of binding compositions complex the target entities to form a complexed population of target entities in the chamber, (iii) a pore size of the second pored member is impervious to the complexed population of target entities, and (iv) the first and second moieties are antibodies or fragments thereof.

8. The device according to claim 7, wherein the pore size of the first pored member is impervious to the complexed population of target entities.

9. The device according to claim 7, wherein the first and second moieties interact with the same or different recognition motif.

10. The device according to claim 7, wherein the first and second moieties are conjugated directly to one another or held together by third and fourth moieties, and the third and fourth moieties are antibodies or fragments thereof.

11. The device according to claim 7, wherein the first outlet and the second inlet are connectable thereby forming the chamber.

* * * * *